United States Patent [19]
Pinchuk et al.

[11] Patent Number: 5,116,360
[45] Date of Patent: May 26, 1992

[54] MESH COMPOSITE GRAFT

[75] Inventors: Leonard Pinchuk; John B. Martin, Jr., both of Miami; Bruce A. Weber, Pembroke Pines, all of Fla.

[73] Assignee: Corvita Corporation, Miami, Fla.

[21] Appl. No.: 634,425

[22] Filed: Dec. 27, 1990

[51] Int. Cl.$^5$ .............................................. A61F 2/06
[52] U.S. Cl. ........................................ 623/1; 623/11; 623/12
[58] Field of Search ..................................... 623/12, 1

[56] References Cited

U.S. PATENT DOCUMENTS 4,475,972 10/1984 Wong .
4,969,896 11/1990 Shors ........................................ 623/1

Primary Examiner—David Isabella
Assistant Examiner—Debra S. Brittingham
Attorney, Agent, or Firm—Lockwood, Alex, FitzGibbon & Cummings

[57] ABSTRACT

A mesh composite graft including an inner component, an outer component formed from strands of durable material, such as polyethylene terephthalate, and an intermediate component made from strands of bicompatible synthetic material having a melting point less than that of the durable material from which the outer component is formed and less than that of the biocompatible synthetic material from which the inner component of the graft is formed. By heating the graft to a temperature grater than the melting point of the material from which the intermediate component is formed but less than the melting point of the outer component material and less than the melting point of the material from which the inner component is formed, the components are bound by the melted intermediate component to provide a totally porous, compliant composite graft reinforced by the outer component.

19 Claims, 1 Drawing Sheet

MESH COMPOSITE GRAFT

BACKGROUND AND DESCRIPTION OF THE INVENTION

The present invention generally relates to implantable prostheses and the like and to methods for making same. More particularly, the invention relates to a graft, such as a vascular graft or AV-shunt, having a compliant porous inner component and a compliant porous load-bearing outer component, bound together by a porous intermediate component that is made of material having a melting point lower than that of the materials from which the inner and outer components are made. With the outer component bound by the intermediate component to the inner component, a porous, yet strengthened integral graft results.

Blood vessels are not straight, rigid tubes but elastic conduits made of a variety of materials and having a compliance that varies with functional considerations. For example, the venous system functions, in part, as the blood reservoir for the body. In order to be able to respond to a larger volume of blood sent into the system because of, for example, a change in arterial blood pressure, the vessels of the venous system must be sufficiently compliant so that they can distend. The arterial system functions as the body's pressure reservoir. In order to avoid the wide swings in the blood pressure and flow that are possible with every contraction and relaxation of the heart, yet be able to maintain sufficient blood pressure so that blood can be pushed into all regions of the body, including through the small-diameter arterioles and the microcirculatory bed, the arteries must have sufficient compliant strength to elastically expand and recoil without the marked distension of the venous system.

Conventional grafts, however, are generally made of materials and in shapes that provide a structure whose compliance is markedly different from that of the walls of the vessel to which they may be attached. Grafts having walls less compliant than that of the host vessel walls are problematic in that conditions, such as intimal hyperplasia and stenotic narrowing, may develop. Grafts with walls having greater compliance than that of the vessel to which the graft is attached are problematic in that a portion of the graft wall may balloon—that is, develop an aneurysm—after implantation.

Other known grafts, while they may be compliant, may not necessarily be made from biocompatible materials. The implantation of a graft made from such material may prompt a thrombogenic or immunological response with the resultant deleterious formation of microthrombi or microocclusions in and around the graft. Other grafts are made from generally non-porous materials, that, accordingly, do not facilitate the ingrowth of cells and tissue within the graft. The full incorporation of the graft into the surrounding host tissue is thereby frustrated. Still other conventional grafts are made from microporous textiles that require preclotting of the vessel wall with blood to prevent leakage of blood at implantation.

A demand therefore is present for an integral graft made from biocompatible materials and having a structure that has compliant strength similar to that of natural tissue but that is sufficiently porous so that the graft may become incorporated into the host tissue yet not leak blood. The present invention satisfies the demand.

The present invention includes a three component system, an inner component, an intermediate component, and an outer component. While the components may be made from materials having generally different melting points and different mechanical properties, at a minimum the inner component and outer component are made from a material or materials having a melting temperature higher than the material from which the intermediate component is made. More specifically, the inner component is porous and is made from a biocompatible synthetic material, preferably a polyurethane composition made with an aromatic polycarbonate intermediate, having a melting point that is, at a minimum, in excess of the melting point of the composition from which the intermediate component is formed (further discussed below).

There are many methods by which the inner component may be made, such as the many known methods used to produce porous compliant vascular prostheses. One such method is termed phase inversion or separation which involves dissolving a urethane in a solvent, such as dimethyl acetamide (DMA), forming a coat on a mandrel—such as by dipping the mandrel into the dissolved urethane—and then immersing the urethane coating in a solution such as water by which DMA may be dissolved, but not urethane, thereby causing the urethane to bead-up and form a porous matrix.

Another method by which the inner component may be formed is termed particle elution. The method utilizes water soluble particles such as salt (NaCl, MgCl2, CaCo2, etc.) polymers, such as polyvinylpyrrolidone, sugars etc. The particles are mixed or blended into a urethane composition, and after forming a graft from the mixture such as by dip coating or extruding the particle filled plastic, the particle is eluted out with a suitable solvent.

Additional methods include replamineform, that involves the dissolution of a matrix, such as that of a sea urchin, out of the urethane with hydrochloric acid, spray techniques where filaments or beads of urethane are sprayed onto a mandrel to produce a porous vascular graft, and electrostatic deposition of urethane fibers from solution.

However, the porous vascular graft preferred in this invention is prepared according to the method detailed in U.S. Pat. No. 4,475,972 to Wong. This patent is incorporated hereinto by reference. An antioxidant may be added to further prevent degradation of the fibers drawn of the material from which the inner component is made.

Regardless of the nature and method of manufacturing the porous inner component, the intermediate component is comprised of one or more layers of a biocompatible synthetic material, preferably a polyurethane material, having a melting point lower than the melting point of the material from which the inner component is formed and lower than the melting point of the material from which the outer component is made.

The outer component comprises a mesh network made of strands, fibers, beads or expanded versions of a durable material such as a composition of fluorocarbons, such as expanded polytetrafluoroethylene ("ePTFE")—commonly termed Teflon—or stable polyesters, such as preferably polyethylene terephthalate ("PET")—commonly termed Dacron. This material is preferably warp-knitted in a tricot or double tricot pattern and shaped in a tubular configuration. It can also be appreciated that the outer component can be woven, braided, weft-knitted and the like with loose fibers, textured fibers and the like to provide increased compliance. With the three components in place, a composite graft according to the present invention is formed by heating the structure to a temperature at or above the melting point of the material from which the intermediate component is formed but below the melting temperature or temperatures of the material from which the outer component is formed and of the material from which the inner component is formed. In this temperature range, the intermediate component may melt without the melting of either the inner component and the outer component, thereby mechanically bonding the inner component to the outer component.

The multi-component system of the present invention provides a number of advantages over conventional grafts. The use of a durable material, such as PET or ePTFE, from which the outer component may be formed is advantageous because of the known strength that such material has in the body. Devices made from PET or ePTFE when implanted in the body are known to maintain their integrity for some three decades. Further advantageously, it has been found that a graft—made according to the present invention and in which PET is used to form the outer component—has a burst strength and a tensile strength that is some two times greater than that of a conventional graft. Such strength prevents the dilation of the vessel in response to, for example, an increase in blood flow and/or pressure, creep relaxation of the urethane, biodegradation of the urethane, plasticization of the urethane, etc. Decreases in the strength of PET that may occur after implantation due, for example, to the absorption of water after implantation, are minimal as Dacron has a low water absorption ability.

The use of a knitted pattern according to which the durable strands of the outer component may be configured is advantageous due to the increased compliance such a pattern provides. As stated above, a durable material such as PET is recognized as a strong yet not necessarily compliant material. However, by knitting the strands from which the outer component is formed into a network, a compliant reinforcing outer component is formed. The use of such a material from which to form the outer component in the three component system of the present invention advantageously provides a strengthened, yet compliant graft.

The winding of strands of synthetic material, such as polyurethane over a mandrel to form an inner component is further advantageous because of the resultant porosity of the component. While the intermediate component may be made porous, for example, by painting synthetic material over the inner component and utilizing the phase inversion method or the particle elution method to form a porous matrix, preferably the intermediate component is formed by winding strands of synthetic material, such as polyurethane over the inner component, to provide a highly porous network. Utilizing strands of PET configured in a knitted pattern to form the outer reinforcement component further provides a porous network. Advantageously, by combining these individually porous components together in a composite graft, a totally porous integral graft results. Porosity is an advantage in medical devices, such as vascular grafts, because an open structure allows vascular fluid to infiltrate and communicate to and from the surrounding tissue and the interior of the graft and allows the ingrowth of tissue to occur within the graft. Accordingly, the device becomes better incorporated into the surrounding tissue, thereby further securing the device within the implantation site.

Uniting the three components into a single composite graft advantageously facilitates the use of the device. The graft may be implanted without the need for any assembly immediately prior to use. The graft may be also cut and/or sutured as a unit without the need for the separate cutting and/or suturing of each component. Methods for cutting the composite graft include scalpel, scissors, hot wires, shaped blades, and the like. The speed with which the graft may be implanted is a particularly distinct advantage since the device is implanted only when a patient is undergoing surgery.

The use of a polycarbonate intermediate rather than, for example, a polyether urethane to make the polyurethane material from which the inner component is preferably made is advantageous as the resultant inner component better resists degradation. The resistance to degradation is further aided by the addition of antioxidant to the material from which the inner component is formed.

It is, accordingly, a general object of the present invention to provide an improved graft.

Another object of the present invention is to provide an integral improved graft made from a composite of layers of synthetic materials.

It is also an object of the present invention to provide a graft that is totally porous thereby facilitating the incorporation of the graft into the site of implantation.

An additional object of the present invention is to provide an improved graft having an outer component which strengthens the device without significantly impairing the overall compliance of the graft.

These and other objects, features and advantages of this invention will be clearly understood and explained with reference to the accompanying drawings and through a consideration of the following detailed description.

BRIEF DESCRIPTION OF THE DRAWINGS

In the course of this description, reference will be made to the attached drawings, wherein.

DESCRIPTION OF THE PARTICULAR EMBODIMENTS

Figure 1:
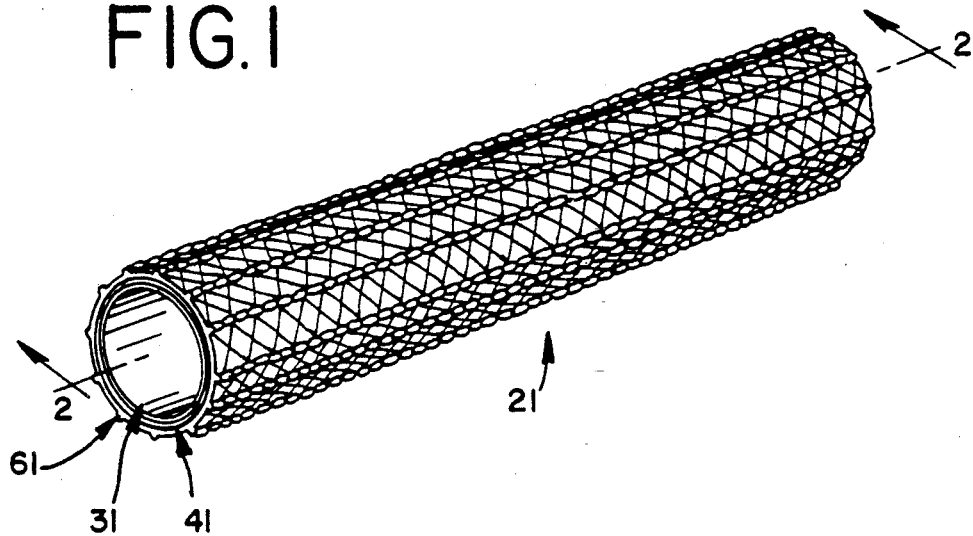
FIG. 1 is a perspective view illustrating an embodiment of a composite vascular graft according to the present invention with an outer component of knitted durable material positioned over and bound by an intermediate component to an inner component.
Figure 2:
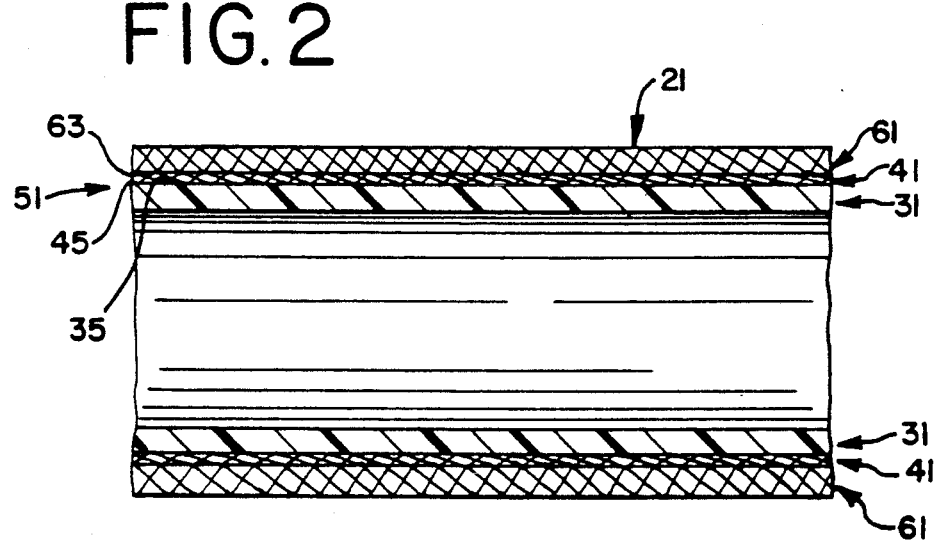
FIG. 2 is a cross sectional view of the composite vascular graft according to the present invention illustrated in FIG. 1.

The present invention is a composite vascular graft—generally designated as 21 in FIGS. 1 and 2—comprised of an inner component 31, an intermediate component 41, and an outer component 61. The inner component will be described first.

Inner component 31 is fabricated from a biocompatible synthetic material, preferably polyurethane, having a melting temperature that is, at a minimum, greater than the melting temperature of the material from which the intermediate component is formed. Preferably, in those embodiments in which the inner component 31 is formed from polyurethane, it is made with an aromatic polycarbonate urethane. Polycarbonate urethanes are preferred over polyether urethanes due to their superior biostability. The aromatic polycarbonate urethanes have melting points in the range of 150° C. to 230° C. This is in contrast to some aliphatic polycarbonate urethanes that have melting points between 90° C. and 130° C. It can also be appreciated that the inner member may be composed of non-urethane materials such as silicone rubber, polyolefins, fluoroelastomers, ePTFE, and the like. An antioxidant, such as Irganox 1010, may be added to the inner member to further prevent degradation of the strands from which the inner component is formed. The melting temperature of the material from which the inner component is preferably formed exceeds 150° C.

The methods by which the inner component 31 may be fabricated include those disclosed in U.S. Pat. No. 4,475,972 to Wong. According to a fabrication method taught in the Wong patent, termed "solution processing", the inner component material is dissolved in a solvent and forced out of one or more orifices to form one or more continuous fibers. The fibers are drawn directly onto a rotating mandrel. As the distributor or spinnerette reciprocates along the mandrel, non-woven strands are layered on top of each other to form porous, non-woven network of criss-crossing strands.

The intermediate layer 41 is formed of a biocompatible synthetic material, such as a polyolefin, a silicone thermoplastic material, etc., or preferably a polyurethane material having a melting temperature less than that of the materials from which the inner and outer components are formed. The intermediate layer can be drawn in the manner described in the Wong patent so that at least one fibrous layer is laid over the inner component 31 to form a porous intermediate layer. This intermediate layer can be spun from solution as described in the Wong patent or can be simply wound onto the inner layer from a spool of the biocompatible low melting point material. Alternatively, phase inversion or particle elution methods may be used to form a porous intermediate component. Examples of suitable low melting point biocompatible materials include the aliphatic polycarbonate or polyether urethanes with melting points of 90° C. to 130° C. The resultant porous, non-woven network of strands forming the intermediate component 41, as drawn over the inner component 31 form a unit 51 which facilitates the transmission of fluid.

Mesh 61, composed of strands of durable material, such as PET or ePFTE, knitted or woven in a generally elongated cylindrical shape and whose inner surface 63 is of a diameter equal to or slightly larger than the diameter of the outer surface 45 of the intermediate component 41, is fitted over the intermediate component 41. To provide compliance to the mesh network of strands from which the outer component is formed, the strands are configured preferably in a knitted pattern. Tricot or double tricot warp knit patterns are preferred. Double tricot patterns are further advantageous because they provide greater depth to the outer component 61 and thereby facilitate the acceptance of and retention of sutures and tissue ingrowth through the graft 21. Tricot or double tricot warp patterns are further advantageous in that they are generally more interlocking than other patterns and therefore resist "running". Other acceptable patterns according to which the strands of the outer component 61 may be formed include jersey or double jersey patterns, woven or braided and multiple layers of the above. Also, the fibers comprising the outer structure may be textured or non-textured and be of a variety of deniers.

The outer component 61 as positioned over the inner component and intermediate component is heated to a temperature equal to or greater than the temperature at which the material from which the intermediate component 41 is formed melts but less than the temperature and/or temperatures at which the material or materials from which the outer component and from which the inner component 31 is formed melts. When the inner component 31 is formed from the preferred material described above, the components are heated to a temperature less than 150° C. but greater than the temperature at which the material from which the intermediate component 41 is formed melts, such as 110° C. By maintaining the three components at such a temperature for a period of time, such as ten minutes, the intermediate component melts thereby securing the outer component 61 and the inner component 31 to each other. To further ensure the secure full engagement of the outer component 61 by the melted intermediate component 41, the outer component 61 may be forcefully pressed into the intermediate component 41 during the heating step such as mechanically and/or with or under pressure. After heating, the united three components are cooled thereby providing an integral mesh composite graft 21.

A mesh composite graft 21 according to the present invention is totally porous and compliant, yet advantageously includes a load bearing component, the outer component 61, which adds strength to the graft and prevents the failure of the graft even in response to greater fluid volume pressures from within, creep relaxation of the inner member and possible biodegradation effects of the inner member.

The advantageous compliance of the composite graft may be adjusted by varying the number of strands from which the inner component and the intermediate component 41 are formed. The compliance of the composite graft 21 may be adjusted also by varying the materials from which the inner component 31 and the intermediate component 41 are formed while maintaining the relationship that the intermediate component 41 must melt at a lower temperature than the materials from which the outer component and the material from which inner component 31 is formed. The compliance of the mesh composite graft 21 may be adjusted further by adjusting the angle at which the strands of the inner component 31 and/or the strands of the outer component 61 are laid down—a higher angle provides a less compliant component and thereby a less compliant graft.

The compliance may be adjusted even further by altering the knitting parameters, such as courses and wales per inch, the stitch density, the fiber denier, the number of strands per filament, the composition of the fibers and filaments such as a mixture of PET and Spandex compositions and whether the outer member is knitted, woven or braided.

The advantageous overall porosity of the graft 21 may be adjusted also in a number of ways. In addition to varying the size and number of the strands from which the inner component 31 and intermediate component 41 are formed, the strands of each component may be drawn at different angles to provide decreased pore size and resultant decreased porosity. Similarly, the porosity of the outer component 61, and thereby the porosity of the composite graft 21 may be varied by varying the size and/or number of the strands and stitch density used to make the outer component mesh.

It can also be appreciated that the outer component need not be a tube formed specifically for this purpose from materials as above but can also be made from a vascular graft preformed from a porous matrix material such as ePTFE. One such graft is manufactured by W. L. Gore and marketed as a Gore-Tex graft. The ePTFE graft may be sheathed over the previously described inner and intermediate components and heat fused into a similar composite graft described in this document. Similarly, the inner members may be a Gore-Tex graft, the intermediate component, a heat fusable thermoplastic, and the outer component, a Dacron knit.

Regardless of the configuration of the inner, intermediate and outer components of the graft, i.e. be it spun, salt eluted, phase inverted, wound with an outer PET mesh, or in which an ePTFE configuration is utilized, the resultant composite graft 21 as formed may be implanted in vascular locations and retained in place through conventional methods, such as suturing. The preferred use of PET, knitted in a preferred tricot or double tricot pattern, from which to make the outer component 61 of the graft 21 provides a graft having a greater thickness than grafts without such a load bearing component. The outer component 61 facilitates the greater retention of the sutures within the graft.

It will be understood that the embodiments of the present invention as described are illustrative of some of the applications of the principles of the present invention. Modifications may be made by those skilled in the art without departure from the spirit and scope of the invention.

We claim:

1. A composite graft for implantation within a host, comprising:

an inner component made from wound, criss-crossing layers of fibers of a first biocompatible synthetic material and shaped to form a porous generally elongated cylindrical shape having a lumen through which blood may flow, said inner component having an outer surface;

an intermediate compliant bonding component made from wound, criss-crossing layers of fiber of a second biocompatible synthetic material, said second material having a melting point lower than the melting point of said first material and lower than the melting point of polyethylene terephthalate, said intermediate component positioned generally over and substantially covering said outer surface of said inner component, said intermediate component being porous and having an outer surface;

said intermediate component as positioned over said outer surface of the inner component forming a fluid transmission unit;

an outer component made from a mesh formed from strands of matrices of durable material, said strands or matrices preformed in a generally elongated cylindrical shape having a lumen therethrough and a diameter which is approximately equal to the outside diameter of said intermediate component, said outer component is positioned over and substantially covering said outer surface of the intermediate component; wherein each said outer component and said inner component is bonded to said intermediate component when each of the components is heated to a temperature less than the melting temperature of said firs material and said durable material thereby securing said components to each other to form a totally porous mesh composition graft.

2. The mesh composite graft according to claim 1, wherein said biocompatible synthetic material from which said inner component is made is polyurethane.

3. The mesh composite graft according to claim 2, wherein said polyurethane is made with a polycarbonate intermediate.

4. The mesh composite graft according to claim 2, wherein said polyurethane is made with an aromatic polycarbonate urethane.

5. The mesh composite graft according to claim 1, wherein said biocompatible synthetic material from which said inner component is made is silicone rubber.

6. The mesh composite graft according to claim 1, wherein said biocompatible synthetic material from which said inner component is made is a polyolefin.

7. The mesh composite graft according to claim 1, wherein said biocompatible synthetic material from which said inner component is made is a fluoroelastomer.

8. The mesh composite graft according to claim 3, wherein said polyurethane includes an antioxidant to prevent degradation of said inner component.

9. The mesh composite graft according to claim 1, wherein said biocompatible synthetic material from which said intermediate component is made is polyurethane.

10. The mesh composite graft according to claim 9, wherein said polyurethane is an aliphatic polycarbonate.

11. The mesh composite graft according to claim 1, wherein said biocompatible synthetic material from which said intermediate component is made is a polyolefin.

12. The mesh composite graft according to claim 1, wherein said biocompatible synthetic material from which said intermediate component is made is a silicon thermoplastic material.

13. The mesh composite graft according to claim 1, wherein said outer component is further secured to said fluid transmission unit by pressing said outer component into said intermediate component during heating.

14. The mesh composite graft according to claim 1, wherein said mesh is formed by knitting said strands of polyethylene terephthalate.

15. The mesh composite graft according to claim 1, wherein said mesh is formed by knitting said strands of polyethylene terephthalate in a tricot pattern.

16. The mesh composite graft according to claim 1, wherein said mesh is formed by knitting said strands of polyethylene terephthalate in a double tricot pattern.

17. The mesh composite graft according to claim 2, wherein said mesh is formed from strands of expanded polytetrafluoroethylene.

18. The mesh composite graft according to claim 2, wherein said mesh is preformed from strands of polytetrafluoroethylene.

19. The mesh composite graft according to claim 2, wherein said mesh is a preformed porous matrix of expanded polytetrafluoroethylene.

* * * * *